(12) United States Patent
Cao et al.

(10) Patent No.: US 11,304,678 B2
(45) Date of Patent: Apr. 19, 2022

(54) SYSTEMS, METHODS, AND APPARATUSES FOR CONFIDENCE MAPPING OF SHEAR WAVE IMAGING

(71) Applicant: KONINKLIJKE PHILIPS N.V., Eindhoven (NL)

(72) Inventors: Ji Cao, Bothell, WA (US); Lars Jonas Olsson, Woodinville, WA (US); Vijay Thakur Shamdasani, Kenmore, WA (US); David Wesley Clark, Derry, NH (US); Hua Xie, Cambridge, MA (US); Jean-Luc Francois-Marie Robert, Cambridge, MA (US); Alexey Viktorovich Cherepakhin, Lake Forest Park, WA (US); Bruce Adrian Kincy, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 369 days.

(21) Appl. No.: 16/476,785

(22) PCT Filed: Jan. 9, 2018

(86) PCT No.: PCT/EP2018/050405
§ 371 (c)(1),
(2) Date: Jul. 9, 2019

(87) PCT Pub. No.: WO2018/130503
PCT Pub. Date: Jul. 19, 2018

(65) Prior Publication Data
US 2019/0357886 A1    Nov. 28, 2019

Related U.S. Application Data

(60) Provisional application No. 62/475,962, filed on Mar. 24, 2017, provisional application No. 62/444,403, filed on Jan. 10, 2017.

(51) Int. Cl.
*A61B 8/00* (2006.01)
*A61B 8/08* (2006.01)
*A61B 8/14* (2006.01)

(52) U.S. Cl.
CPC ............ *A61B 8/463* (2013.01); *A61B 8/0858* (2013.01); *A61B 8/14* (2013.01); *A61B 8/483* (2013.01);
(Continued)

(58) Field of Classification Search
CPC .................................................. G06T 7/0012
See application file for complete search history.

(56) References Cited

U.S. PATENT DOCUMENTS

| | | |
|---|---|---|
| 2013/0218011 A1 | 8/2013 | Benson et al. |
| 2015/0164480 A1 | 6/2015 | Watanabe et al. |
| 2015/0327838 A1* | 11/2015 | Francis ................ A61B 8/5276 600/450 |

FOREIGN PATENT DOCUMENTS

| | | | |
|---|---|---|---|
| CN | 104605891 A | * | 5/2015 |
| WO | 2016067072 A1 | | 5/2016 |

OTHER PUBLICATIONS

International Search Report and Written Opinion for International Application No. PCT/EP2018/050405, filed Jan. 9, 2018, 14 pages.

* cited by examiner

*Primary Examiner* — Boniface Ngathi

(57) ABSTRACT

Systems, methods, and apparatuses for confidence mapping of shear wave measurements are disclosed. Confidence maps of shear wave image measurements may be generated from one or more confidence factors. Masking of graphical overlays of tissue stiffness values, based at least in part on the confidence map is disclosed. The confidence map and/or
(Continued)

masked graphical overlays of tissue stiffness values may be superimposed on ultrasound images and provided on a display.

15 Claims, 5 Drawing Sheets

(52) U.S. Cl.
CPC ............ *A61B 8/485* (2013.01); *A61B 8/5207* (2013.01); *A61B 8/5253* (2013.01); *A61B 8/5276* (2013.01)

SYSTEMS, METHODS, AND APPARATUSES FOR CONFIDENCE MAPPING OF SHEAR WAVE IMAGING

RELATED APPLICATIONS

This application is the U.S. National Phase application under 35 U.S.C. § 371 of International Application No. PCT/EP2018/050405, filed on Jan. 9, 2018, which claims the benefit of both Provisional Application Ser. No. 62/475,962, filed Mar. 24, 2017, and Provisional Application Ser. No. 62/444,403, filed Jan. 10, 2017. These applications are hereby incorporated by reference herein.

BACKGROUND

Shear wave imaging is a technique for measuring tissue stiffness. In an example method for performing shear wave imaging, an initial ultrasound pulse, referred to as a push pulse, is applied to a tissue. The tissue may respond to the force of the push pulse by deforming. This deformation may propagate through the tissue as one or more waves, referred to as shear waves. The propagation of the shear wave or waves through the tissue is monitored by additional ultrasound pulses, referred to as tracking pulses. Other methods of shear wave imaging may also be used. For example, the tissue may be deformed by using external vibration, such as by physically depressing the tissue, and rapidly acquiring images of the surrounding tissue. The images are then analyzed to detect and monitor the resulting shear wave or waves.

Based on one or more factors (e.g., shear wave velocity, shear wave magnitude, and/or maximum propagation distance), a stiffness value of the tissue is calculated. An example of a stiffness value is the elastic modulus (E), typically measured in kPa. One method of calculating the elastic modulus is $E=3\rho(V_s)^2$, where $V_s$ is the shear wave propagation velocity in m/s and $\rho$ is tissue density. Other methods of calculating a stiffness value of the tissue may be used. For example, the shear wave propagation velocity alone may be used as a measure of tissue stiffness.

Tissue stiffness measurements may be useful in disease diagnosis and/or monitoring. For example, in cirrhosis of the liver, diseased liver tissue has a higher stiffness than healthy liver tissue. Accordingly, shear wave imaging may be used to diagnose or monitor liver disease. This may allow for improved diagnosis, monitoring and/or a reduction in the number of biopsies required. Similarly, shear wave imaging may be used to diagnose or monitor other diseases.

Shear wave imaging is still a relatively new technique. Many ultrasound technicians and/or clinicians may be unfamiliar with how to acquire reliable shear wave measurements and/or how to interpret shear wave measurement results. Furthermore, in some areas of the world (e.g., developing countries), there is a shortage of skilled ultrasound technicians to assist clinicians in acquiring and interpreting ultrasound images such as ultrasound images that include shear wave data. Thus, there is a need for tools that can assist ultrasound technicians and clinicians in utilizing shear wave imaging, which may improve patient care.

SUMMARY

According to an exemplary embodiment of the disclosure, an ultrasound imaging system may include an ultrasound imaging device configured to generate shear wave signals responsive to shear wave tracking echoes received by an ultrasound probe communicatively coupled to the ultrasound imaging device and a processor integral with or communicatively coupled to the ultrasound imaging device. The processor may include a shear wave processor configured to calculate tissue stiffness values based, at least in part, on the shear wave signals, a confidence map generator configured to calculate confidence values based on at least one confidence factor, and an image processor configured to generate an ultrasound image including a graphical overlay of tissue stiffness values for one or more pixels within a region of interest, and wherein the ultrasound image is configured to provide, based on the calculated confidence values, an indication of reliability of the tissue stiffness values within the region of interest. In some embodiments, the ultrasound imaging system may further include a display communicatively coupled to the image processor, wherein, responsive to the image processor, the display is configured to display concurrently the image with the masked graphical overlay of tissue stiffness values superimposed and the image with the a confidence map superimposed, wherein the confidence map is based, at least in part, on the confidence values.

According to an exemplary embodiment of the disclosure, a method may include calculating a confidence factor for each of a plurality of pixels, determining a confidence value for each of the plurality of pixels based, at least in part, on the corresponding confidence factor, wherein the confidence values correspond to confidence in tissue stiffness values, and generating a confidence map based, at least in part, on the confidence values. In some embodiments, the method may further include acquiring a shear wave image and calculating a tissue stiffness value for each pixel in the shear wave image. In some embodiments, calculating the confidence factor comprises calculating a plurality of confidence factors for each of the plurality of pixels, and calculating the confidence value for each of the plurality of pixels comprises combining the plurality of confidence factors for each of the plurality of pixels.

DETAILED DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Many factors can influence the quality of an image and/or reliability of ultrasound measurements. For example, poor contact between an ultrasound probe and the skin of a patient can lead to poor image quality or no image at all. A patient breathing or an ultrasound technician shaking an ultrasound probe can lead to image artifacts. In shear wave imaging, shear waves may be no more than a few microns in magnitude, and noise from patient or technician movement could completely overwhelm the shear wave signal. Blood flow and fluid pockets in tissue may also interfere with shear wave data. An experienced ultrasound technician may recognize poor image quality or artifacts and know when to attempt to reacquire an image. The experienced ultrasound technician may also know not to collect measurements in a certain area to avoid unreliable data. However, an inexperienced user may not recognize poor image quality or areas where data is unreliable. This may lead to the inexperienced user to acquiring images of poor diagnostic value or collecting misleading measurements.

According to embodiments of the disclosure, an ultrasound imaging system may provide graphical representations of data and/or graphical representations of confidence in the data to assist users in recognizing when imaging may need to be repeated and/or where reliable measurements can be acquired.

Figure 1:
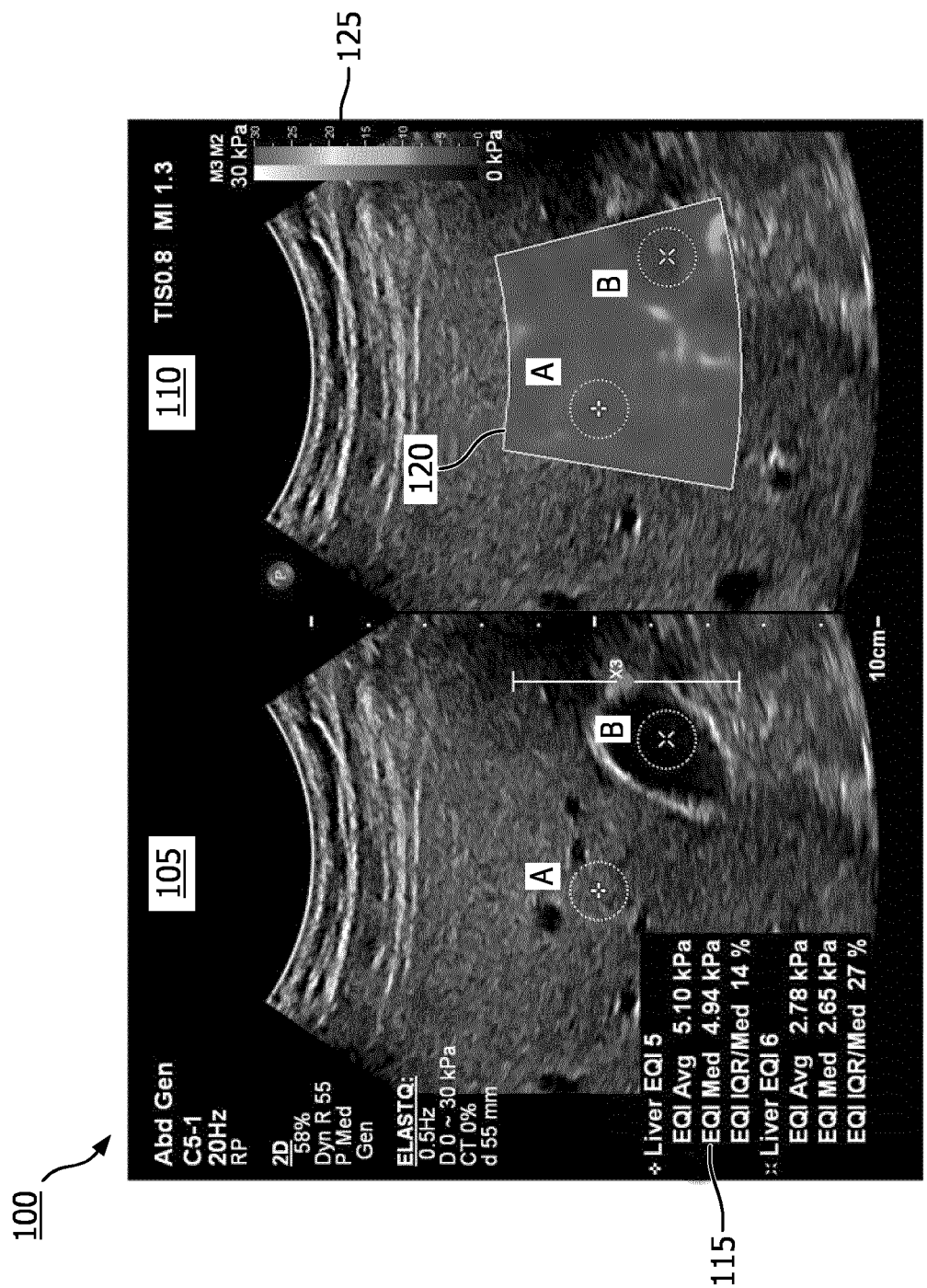
FIG. 1 shows example screen shots of ultrasound images of a liver that includes shear wave data.

FIG. 1 shows an example screen shot 100 of ultrasound images 105, 110 of a liver that includes shear wave data, which may be generated and displayed by an ultrasound imaging system according to the present disclosure. Ultrasound images generated by systems according to the present disclosure may display tissue stiffness values, for example as discrete values at any given (e.g., user selected) location in the imaged region or as a color-coded map over a user-selected region of interest (ROI) within the imaged region. Ultrasound images 105, 110 illustrate examples of these two example scenarios, with image 105 displaying the tissue stiffness values as discrete values and image 110 displaying the tissue stiffness value in the form of a color-coded map. In some examples, separate images, each including tissue stiffness information, may be shown concurrently on a display or only one of the ultrasound images may be displayed. In other examples, a single image may be displayed which includes both the display of tissue stiffness discrete values and a color-coded map of the ROI. In the illustrated example, ultrasound image 105 includes two pointers A and B. The pointers A, B may have been placed on the respective image responsive to input by a user, such as an ultrasound technician or a clinician. As will be described further below the ultrasound imaging system may be configured to calculate tissue stiffness values and may provide an indication of the tissue stiffness values (e.g., in the form of a color map, or by displaying discrete values) on a display (e.g., as an overlay or adjacent to a grayscale (i.e., B-mode) ultrasound image). In the illustrated example, tissue stiffness values (in kPa) for locations in the tissue that correspond to pointers A and B are provided in a box 115, e.g., in the lower left corner of the image. In other examples, the indication may be provided differently (e.g., by annotating the value next to each selected location corresponding to pointers A, B). In the example shown in FIG. 1, the tissue at the location of pointer A has a stiffness value of 5.10 kPa and the tissue at the location of pointer B has a stiffness value of 2.78 kPa. The stiffness values may be calculated from shear wave data acquired by an ultrasound imaging system according to the present disclosure. As will be further described, the ultrasound imaging system may be configured to generate ultrasound images which include an indication of the reliability of the stiffness values (e.g., discrete or overlaid as a color coded map on the image). The indication of the reliability may be provided in the form of a confidence map (not shown in FIG. 1 but described in further detail below). In the illustrated example, the ultrasound image 110 includes a graphical overlay 120 of tissue stiffness values, in the form of a color map, which are calculated based on the shear wave data. In some examples, different tissue stiffness values may be represented by different colors and/or different grayscale values. For example, low stiffness values may be represented by blue pixels while high stiffness values may be represented as orange or red pixels. In the example shown in FIG. 1, the color-coded map representing the tissue stiffness values for the ROI may be associated with a color scale bar 125, which is displayed with the image for interpreting the color-coded map. The graphical overlay of stiffness values may provide the user with a qualitative overview of tissue stiffness over a large area. In contrast, the pointers A and B may provide the user with quantitative stiffness values at specific points. In this illustrated example, a measure of confidence (e.g., an indication of the reliability) of the tissue stiffness values is not displayed and thus the user is left to independently decide whether or not a quality image and/or reliable measurement has been obtained.

An experienced ultrasound user may notice that pointer A is positioned on liver tissue, but pointer B is positioned over the gall bladder. The gall bladder is an inappropriate location to measure tissue stiffness because shear waves may not propagate through the fluid of the gall bladder as they do through tissue. However, an inexperienced user may mistake the gall bladder as a suspicious area in the liver or may not know stiffness values at the gall bladder are unreliable. Neither the ultrasound images 105, 110 nor the graphical overlay 120 of stiffness values provides feedback to the inexperienced user as to which locations in the image include reliable tissue stiffness measurements.

According to at least one embodiment of the disclosure, an ultrasound system may analyze acquired ultrasound images and/or shear wave data to determine the quality of the image and/or reliability of the shear wave data. The ultrasound system may provide an indication of the reliability of the displayed image data and/or information to guide the user in reacquiring an image, which may enable the acquisition of better images and more accurate measurements for patient diagnosis and/or monitoring.

According to at least one embodiment of the disclosure, an ultrasound system may provide a graphical overlay on an ultrasound image that indicates confidence values for tissue stiffness values calculated from shear wave data. In some examples, the confidence values may be presented to the user in a similar format as the calculated tissue stiffness values. For example, the display may be configured to provide the discrete confidence value associated with any discrete tissue stiffness value on the image. In other examples, the confidence values may be provided as a graphical overlay (e.g., a color map) which may be overlaid onto the anatomy image (e.g., a B-mode image, image reconstructed from shear wave measurements). This graphical overlay of confidence values may be referred to as a confidence map. The confidence map may allow a user to easily perceive where tissue stiffness values are most reliable and to take measurements in those areas or reacquire the image if measurements need to be obtained in areas indicated as having unreliable tissue stiffness characterization in the present image. In some examples, the display may be configured to display a single image, which may include a color-map of either the tissue stiffness values as shown on the right-hand side image 110 of FIG. 1 or representative of the confidence values, as shown in other figures. In some examples, two images, one including the color-map of the stiffness values and one image including the color map of the confidence values, are displayed side by side.

In some examples, the confidence values may be used to filter out the tissue characterization data to exclude from displaying tissue stiffness that is below a minimum reliability measure. For example, according to at least one embodiment of the disclosure, the confidence map may be used to mask portions of the tissue stiffness values graphical overlay (e.g., exclude those portions of the tissue stiffness map from being displayed) where confidence in the tissue stiffness values is below a certain threshold value (e.g., 60%). The threshold confidence value may be pre-programmed in the ultrasound system or set by the user. The confidence map masking may guide the user to regions with more reliable tissue stiffness values and/or prevent a user from viewing tissue stiffness values in regions where the confidence value is below the threshold.

Figure 2:
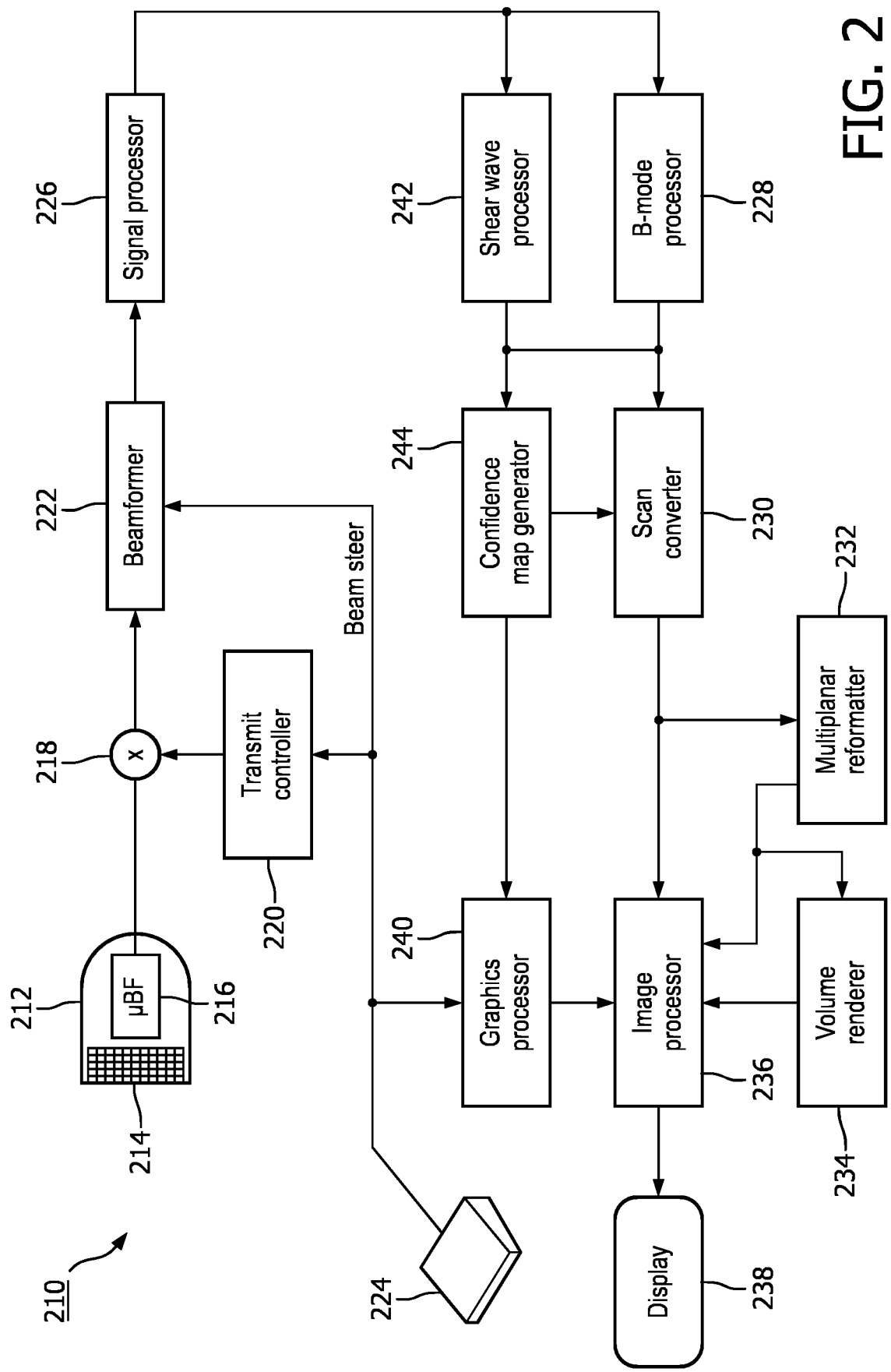
FIG. 2 is a block diagram of an ultrasound imaging system according to an embodiment of the disclosure.

Referring to FIG. 2, an ultrasound imaging system 210 constructed in accordance with the principles of the present invention is shown in block diagram form. The ultrasound imaging system 210 may include an ultrasound imaging device configured to receive a shear wave signal for performing shear wave imaging. The ultrasound imaging device may include processing components (e.g., beamformer, signal processor, etc.) communicatively coupled to an ultrasound probe operable to transmit ultrasound and receive echoes from a subject. For example, in the ultrasonic imaging system of FIG. 2, an ultrasound probe 212 includes a transducer array 214 for transmitting ultrasonic waves and receiving echo information. A variety of transducer arrays are well known in the art, e.g., linear arrays, convex arrays or phased arrays. The transducer array 214, for example, can include a two dimensional array (as shown) of transducer elements capable of scanning in both elevation and azimuth dimensions for 2D and/or 3D imaging. The transducer array 214 is coupled to a microbeamformer 216 in the probe 212 which controls transmission and reception of signals by the transducer elements in the array. In this example, the microbeamformer is coupled by the probe cable to a transmit/receive (T/R) switch 218, which switches between transmission and reception and protects the main beamformer 222 from high energy transmit signals. In some embodiments, the T/R switch 218 and other elements in the system can be included in the transducer probe rather than in a separate ultrasound system base. The transmission of ultrasonic beams from the transducer array 214 under control of the microbeamformer 216 is directed by the transmit controller 220 coupled to the T/R switch 218 and the beamformer 222, which receives input from the user's operation of the user interface or control panel 224. One of the functions controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals are coupled to a signal processor 226. The signal processor 226 can process the received echo signals in various ways, such as bandpass filtering, decimation, I and Q component separation, and harmonic signal separation. The signal processor 226 may also perform additional signal enhancement such as speckle reduction, signal compounding, and noise elimination. The processed signals are coupled to a B mode processor 228, which can employ amplitude detection for the imaging of structures in the body. The signals produced by the B mode processor are coupled to a scan converter 230 and a multiplanar reformatter 232. The scan converter 230 arranges the echo signals in the spatial relationship from which they were received in a desired image format. For instance, the scan converter 230 may arrange the echo signal into a two dimensional (2D) sector-shaped format, or a pyramidal three dimensional (3D) image. The multiplanar reformatter 232 can convert echoes which are received from points in a common plane in a volumetric region of the body into an ultrasonic image of that plane, as described in U.S. Pat. No. 6,443,896 (Detmer). A volume renderer 234 converts the echo signals of a 3D data set into a projected 3D image as viewed from a given reference point, e.g., as described in U.S. Pat. No. 6,530,885 (Entrekin et al.) The 2D or 3D images are coupled from the scan converter 230, multiplanar reformatter 232, and volume renderer 234 to an image processor 236 for further enhancement, buffering and temporary storage for display on an image display 238. The graphics processor 240 can generate graphic overlays for display with the ultrasound images. These graphic overlays can contain, e.g., standard identifying information such as patient name, date and time of the image, imaging parameters, and the like. For these purposes the graphics processor receives input from the user interface 224, such as a typed patient name. The user interface can also be coupled to the multiplanar reformatter 232 for selection and control of a display of multiple multiplanar reformatted (MPR) images.

In accordance with the examples herein, the transducer array 214 is configured to transmit, responsive to control by the transmit controller 220, push pulses to generate a shear wave in tissue. The transducer array 214 may further be operable to transmit and receiving tracking pulses to monitor the shear wave in the tissue. The ultrasound system 210 may acquire shear wave imaging data concurrently with or at a different time (before or after) acquiring or in lieu of B-mode imaging data. For example, the ultrasound system 210 may perform shear wave imaging before or after acquiring a B-mode image. In some embodiments, the ultrasound system 210 may perform shear wave and B-mode imaging at the same time. In some embodiments, the ultrasound system 210 may perform shear wave imaging and B-mode imaging in an interleaved manner. The ultrasound system 210 may display an image based on shear wave imaging rather than B-mode imaging. In some embodiments, the ultrasound system 210 may generate a ultrasound image based on both the shear wave and B-mode imaging data.

During shear wave imaging, the partially beamformed shear wave signals produced by the microbeamformer 216 are coupled to the main beamformer 222 where partially beamformed signals from individual patches of transducer elements are combined into a fully beamformed shear wave signal. The beamformed signals are coupled to the signal processor 226. The signal processor 226 can process the received shear wave signals in various ways, such as band-pass filtering, decimation, signal compounding, and/or noise elimination. The processed shear wave signals may be provided to a shear wave processor 242. The shear wave processor 242 may calculate tissue stiffness values (e.g., shear wave velocity in tissue, elastic modulus) from the shear wave data included in the shear wave signals. A tissue stiffness value may be calculated for each pixel in an ultrasound image.

Processed ultrasound image and/or shear wave signals from the signal processor 226, and/or tissue stiffness values from the shear wave processor 242 may be provided to a confidence map generator 244. The confidence map generator 244 may calculate a confidence value for each tissue stiffness value based on one or more confidence factors. For example, each confidence factor may have a value between 0 and 1, which may represent a confidence from 0-100%.

The confidence map generator 244 may calculate a confidence factor for each pixel in an ultrasound image to determine a confidence value. In some embodiments, two or more confidence factors may be calculated for each pixel and combined to generate a confidence value for the pixel. In some embodiments, the confidence map generator 244 calculates the confidence factors and multiplies the confidence factors together to generate a confidence value for the pixel. In some embodiments, the confidence factors are given different weights when multiplied together. The weights may be selected by a user or predetermined by the ultrasound imaging system. In some embodiments, all of the weights are the same or are omitted.

In one example of calculating confidence values from confidence factors, the confidence map generator 244 may be configured to calculate a confidence value in accordance with equation 1:

$$CV_i = (W_1 \times CF_1) \times (W_2 \times CF_2) \times (W_3 \times CF_3) \times (W_n \times CF_n) \quad \text{Equation 1,}$$

in which, $CV_i$ is the confidence value for a given pixel, $CF_1$ through $CF_n$ are the confidence factors associated with that pixel and $W_1$ through $W_n$ are the weights applied to each confidence factor. In some embodiments, $W_1$ through $W_n$ are omitted from Equation 1. That is, each confidence factor is given equal weight. In further embodiments, a modified equation 1 may be used in which a single overall scaling factor is applied the product of the individual confidence factors. In some embodiments, the confidence map generator 244 compares the value of each confidence factor and selects the confidence factor with the lowest value as the confidence value for the pixel. For example, the confidence map generator 244 may be configured to calculate a confidence value in accordance with equation 2:

$$CV_i = \min(W_1 \times CF_1, W_2 \times CF_2, W_3 \times CF_3, \ldots W_n \times CF_n) \quad \text{Equation 2,}$$

In which the confidence value for a given pixel ($CV_i$) is calculated as the minimum of the confidence factors $CF_1$ through $CF_n$ associated with that pixel and $W_1$ through $W_n$ are the weights applied to each confidence factor. In some embodiments, $W_1$ through $W_n$ are omitted from Equation 2 such that each confidence factor is given equal weight. Any number of confidence factors, for example two or more confidence factors, may be used in embodiments of the present disclosure. Other relationships may be used to define a confidence value in terms of a plurality of confidence factors. If only one confidence factor is used, the value of the confidence factor may correspond to the confidence value.

Confidence factors may include, but are not limited to, signal-to-noise ratio, flow, flash, shear wave displacement amplitude, reconstruction confidence, range estimate, and/or energy ratio.

The signal-to-noise ratio (SNR) may be calculated by any appropriate method. For example, for each pixel in an ultrasound image, a noise floor may be modeled and the average power of a shear wave tracking signal may be determined. The noise model and the tracking signal power may be converted to decibel units (dB) and subtracted. A certain dB value may be chosen as low confidence and a higher dB value may be chosen as high confidence. For example, 20 dB may correspond to 0% confidence and 80 dB may correspond to 100% confidence. In some applications, when the confidence factors are weighted, the SNR confidence factor may be given the most weight.

Flow and flash are both modes of motion detection. Image processing techniques may be used to detect motion during the tracking time of shear wave imaging. If the motion is consistently in one direction, it is considered flow. That is, it is most likely a consistent flow of fluid such as blood in a vessel. If the motion is inconsistent and/or large in magnitude in any direction, it is considered flash. Flash may be caused by either patient or probe movement. Detection of either flash or flow returns low confidence values.

Displacement amplitude is the magnitude of the shear wave as it propagates through tissue in the tracking field. A high magnitude may correspond to high confidence whereas a low magnitude may correspond to a low confidence. What is considered high or low magnitude of a shear wave may depend on the type of tissue that is being examined. In some embodiments, displacement amplitude may be given less weight than SNR and/or motion confidence factors.

Various algorithms are known for reconstructing an ultrasound image from acquired shear wave data. Some reconstruction algorithms produce certainty coefficients in stiffness estimations during reconstruction. The certainty coefficients may be used as confidence factors in some embodiments.

In some embodiments, the ultrasound system may have one or more operation settings that may optimize shear wave imaging based on range estimate of expected tissue stiffness values (e.g., 5-20 kPa, 30-50 kPa). The range estimate may be provided by a user. Optimizations may include, but are not limited to, the strength, timing, spacing and/or shape of push pulses and/or tracking pulses. If the stiffness values calculated by the shear wave processor 242 fall outside the range estimate provided by the user, confidence values may be reduced.

The energy ratio is a measure of the strength of the shear wave signal. One method of calculating the energy ratio includes filtering tissue displacement data to extract the shear wave in the tissue from noise. If the energy remaining in the shear wave signal is low compared to the energy of the unfiltered signal, it may indicate that most of the shear wave data was noise. Accordingly, a low energy ratio corresponds to low confidence and a high energy ratio corresponds to high confidence. In some embodiments, the energy ratio may be converted to decibel units.

In some embodiments, all confidence factors may be used to calculate a confidence value. In some embodiments, only a subset of the confidence factors may be used. For example, in some applications, only SNR, flow, and flash may be used to calculate confidence values. In some applications, where it is unknown if the tissue type is amenable to shear wave analysis, displacement amplitude may be used as a confidence factor. In applications where shear wave amplitudes tend to be low, the energy ratio may be used as a confidence factor. The confidence factors used and/or method of combining the confidence factors to calculate confidence values may be selected by a user or may be predetermined by the ultrasound system.

Returning to FIG. 2, the confidence values output by the confidence map generator 244 may be coupled to the scan converter 230 and/or to the graphics processor 240 to generate a confidence map, i.e., a graphical overlay representing that confidence values at any given pixel within the ROI, which may be superimposed over a background ultrasound image (e.g., a B-mode image or shear wave image). The tissue stiffness values calculated by the shear wave processor 242 may also be provided to the graphics processor 240 to generate a graphical overlay based on tissue stiffness values. In some embodiments, the graphics processor 240 may combine the confidence map and the tissue stiffness values to generate a graphical overlay that masks out tissue stiffness values that have a confidence value below a threshold value (e.g., 60%, 80%, 90%). In some embodiments, the confidence map generator 244 combines the confidence values and tissues stiffness values and provides instructions to the graphics processor 240 regarding which pixels should be masked in the graphical overlay. For example, the confidence map generator 244 may provide only a subset of the tissue stiffness values for the region of interest, which may be selected based on the respective confidence values, to the graphics processor 240 for generating the graphical overlay.

FIG. 2 shows the shear wave processor 242, B-mode processor 228, confidence map generator 244, graphics processor 240, and image processor 236 as separate processors. One or more processors may be implemented using a specifically programmed central processing unit, graphical processing unit, and/or application specific integrated circuit. In some embodiments, the functionality of two or more processors may be combined into one processor. For example, in some embodiments, the functionality of the image processor 236 and graphics processor 240 may be combined into a single processor. In another example, the functionality of the shear wave processor, B-mode processor, and confidence map generator may be combined into a single processor. Other combinations of functionality may also exist. For example, ultrasound imaging system 210 may include an ultrasound imaging device (e.g., array 214) that may be configured to generate shear wave signals responsive to shear wave tracking echoes received by an ultrasound probe 212 communicatively coupled to the ultrasound device. The ultrasound imaging system 210 may include a processor integral with or communicatively coupled to the ultrasound imaging device. The processor may include the shear wave processor 242 configured to calculate tissue stiffness values based, at least in part, on the shear wave, the confidence map generator 244 configured to calculate confidence values based on at least one confidence factor, an image processor 236 configured to generate an ultrasound image including a graphical overlay of tissue stiffness values for one or more pixels within a region of interest, and provide, based on the calculated confidence values, an indication of reliability of the tissue stiffness values within the region of interest.

Figure 3:
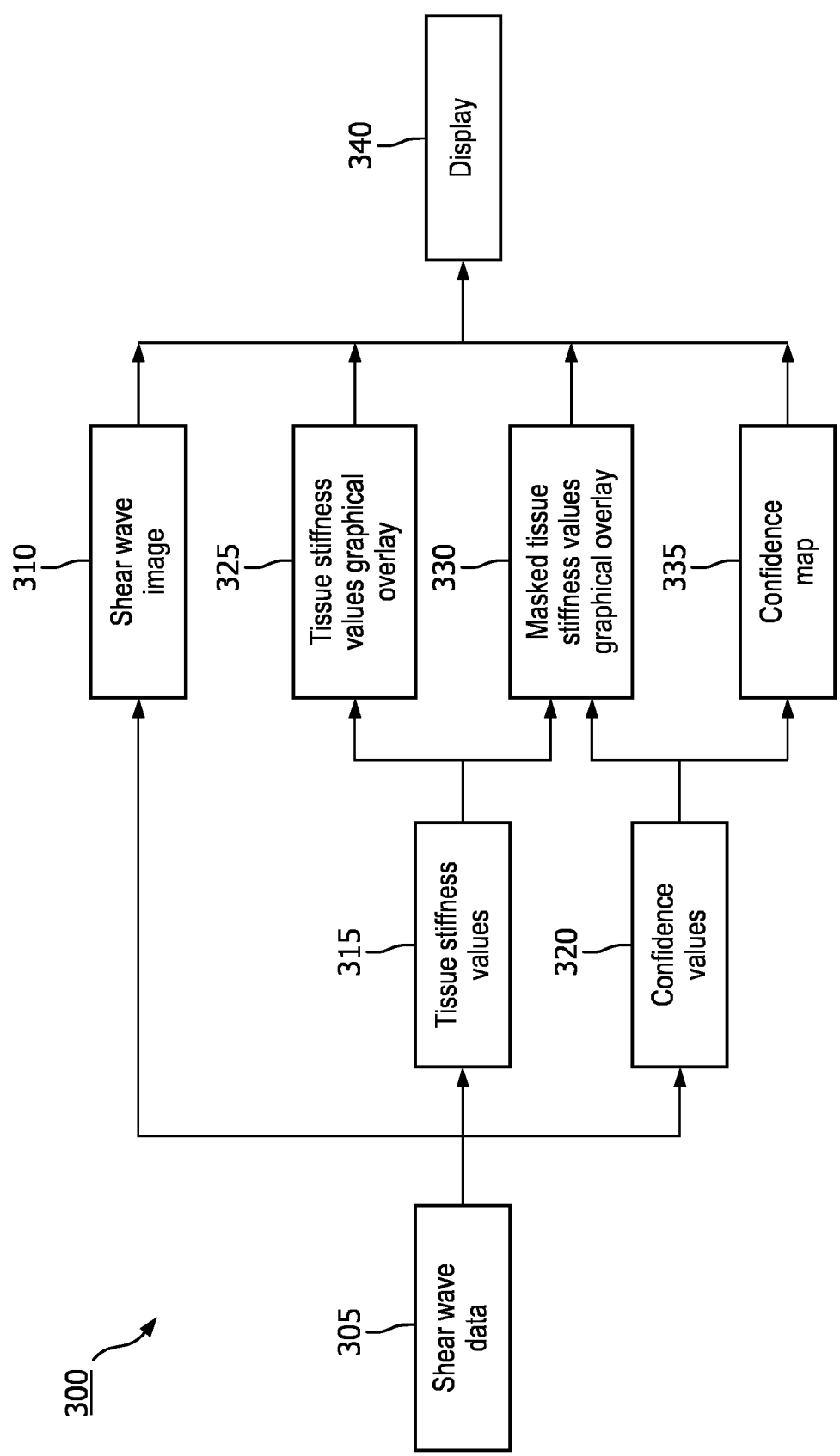
FIG. 3 is a flow chart that illustrates the different images and graphical overlays according to embodiments of the disclosure.

FIG. 3 is a flow chart 300 that illustrates the flow of data between processing components of the ultrasound imaging system for generating images according to embodiments of the present disclosure. Shear wave data 305 may be passed to the shear wave processor 242 for generating tissue stiffness values 315 and a shear wave image 310, and to the confidence map generator 244 for generating confidence values 320. In some embodiments, the shear wave image 310 may additionally or alternatively use a B-mode imaging data for generating the background image (i.e., an image of the anatomy). Tissue stiffness values 315 may be used to generate (e.g., by a graphics processor 240) a graphical overlay of tissue stiffness values 325, such as the graphical overlay shown in FIG. 1. The confidence values 320 may be used to generate (e.g., by confidence map generator 244) a graphical overlay of confidence values, referred to as a confidence map 335. The tissue stiffness values 315 and confidence values 320 may be combined (e.g., by confidence map generator 244 or by graphics processor 240) to generate a masked tissue stiffness value graphical overlay 330. Each of these three overlays may be combined with the shear wave image 310 (e.g., a gray-scale image) to be provided on a display 340, such as display 238 shown in FIG. 2.

Figure 4:
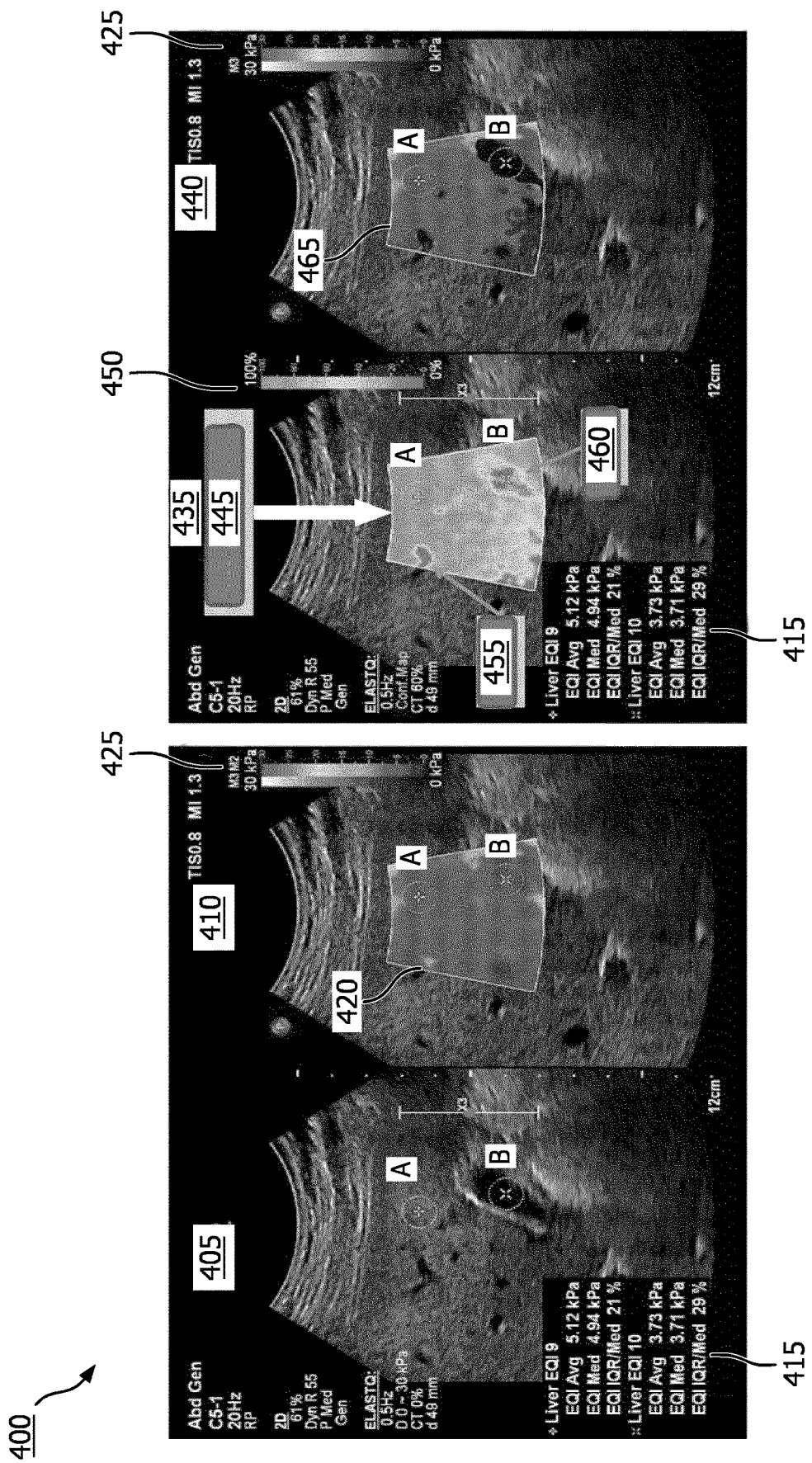
FIG. 4 shows a series of example screen shots ultrasound images and example graphical overlays according to embodiments of the disclosure.

FIG. 4 shows an example screen shots 400 of ultrasound images 405, 410, 435, and 440 and graphical overlays 420, 445, and 465 that include shear wave data, which may be generated and displayed by an ultrasound imaging system according to the present disclosure (e.g., ultrasound imaging system 210 of FIG. 2). Ultrasound image 405 is an image of the liver with blood vessels and the gall bladder. Ultrasound image 405 may have been generated by shear wave imaging data, B-mode imaging data, or a combination thereof. Ultrasound image 405 includes two pointers A and B. The pointers A, B may have been placed on the respective image responsive to input by a user, such as an ultrasound technician or a clinician. The user may have provided the input via a user interface, such as user interface 224 of FIG. 2. The ultrasound imaging system may be configured to calculate tissue stiffness values and may provide an indication of the tissue stiffness values on a display (e.g., display 238 of FIG. 2). In the illustrated example, tissue stiffness values (in kPa) for locations in the tissue that correspond to pointers A and B are provided in a box 415, e.g., in the lower left corner of the image. In other examples, the indication may be provided differently (e.g., by annotating the value next to each selected location corresponding to pointers A, B). In the example shown in FIG. 4, the tissue at the location of pointer A has a stiffness value of 5.12 kPa and the tissue at the location of pointer B has a stiffness value of 3.73 kPa. The stiffness values may have been calculated from the shear wave data by a shear wave processor (e.g., shear wave processor 242 in FIG. 2). The shear wave data may have been acquired by an ultrasound imaging device including an ultrasound probe (e.g., ultrasound probe 212 in FIG. 2).

The ultrasound image 410 includes a graphical overlay of tissue stiffness values 420 over a region of interest (ROI). The ROI may have been selected by a user in some examples. The graphical overlay of tissue stiffness values 420, in the form of a color map, which are calculated based on the shear wave data, superimposed. In some examples, different tissue stiffness values may be represented by different colors and/or different grayscale values. For example, low stiffness values may be represented by blue pixels while high stiffness values may be represented as orange or red pixels. In the example shown in FIG. 4, the color-coded map representing the tissue stiffness values for the ROI may be associated with a color scale bar 425, which is displayed with the image for interpreting the color-coded map. The graphical overlay of stiffness values 420 may provide the user with a qualitative overview of tissue stiffness over a large area. In contrast, the pointers A and B may provide the user with quantitative stiffness values at specific points.

Ultrasound image 435 includes a confidence map 445 superimposed on the ultrasound image in the ROI. The confidence map may have been generated in part from confidence values calculated by a confidence map generator in some examples (e.g., confidence map generator 244 in FIG. 2). Similar to the graphical overlay for tissue stiffness values 420, different confidence values may be displayed in different colors (e.g., green for high confidence, yellow for medium confidence, and red for low confidence) or grayscale values. In the example shown in FIG. 4, the color-coded confidence map representing the confidence values for the ROI may be associated with a color scale bar 450, which is displayed with the image for interpreting the color-coded confidence map. Now with the confidence map 445, a user may see that there are low confidence values at the site of the blood vessel 455 and the gall bladder 460. Even if the user does not recognize the anatomy in the image, the user may be alerted by the ultrasound system not to collect tissue stiffness measurements at those sites.

Ultrasound image 440 is the ultrasound image with a masked graphical overlay of tissue stiffness values 465 superimposed over the ROI. The masked graphical overlay 465 shows tissue stiffness values from the graphical overlay of tissue stiffness values 420 for the areas that have medium to high confidence, based at least in part on the confidence values. However, the tissue stiffness values in low confidence areas have been masked out. Which areas of the graphical overlay of tissue stiffness values 420 are masked out based on the confidence values is determined by a threshold value (e.g., 60%). The threshold value may be pre-set by the ultrasound system or by the user. In some embodiments, the masked graphical overlay may have been generated by a graphics processor and/or an image processor for display (e.g., graphics processor 240 and image processor 236 of FIG. 2) based at least in part on the tissue stiffness values and/or confidence values. In the example shown in FIG. 4, no tissue stiffness values are shown over the vessel and gall bladder. Again, a user is alerted by the ultrasound system not to collect tissue stiffness measurements in the masked areas. In some embodiments, the ultrasound system may prevent the user from collecting stiffness measurements in the masked areas.

In some embodiments, all ultrasound images 405, 410, 435, and 440 may be concurrently presented on a display (e.g., display 238 of FIG. 2). In some embodiments, only one of the ultrasound images may be displayed, and a user may toggle between the images. In some embodiments, two or more images may be displayed concurrently. For example, images 435 and 440 may be concurrently displayed. In another example, images 405 and 440 may be concurrently displayed. Other combinations of images may also be displayed. A user may control which images are displayed and the orientation of the images via a user interface such as user interface 224 shown in FIG. 2.

Figure 5:
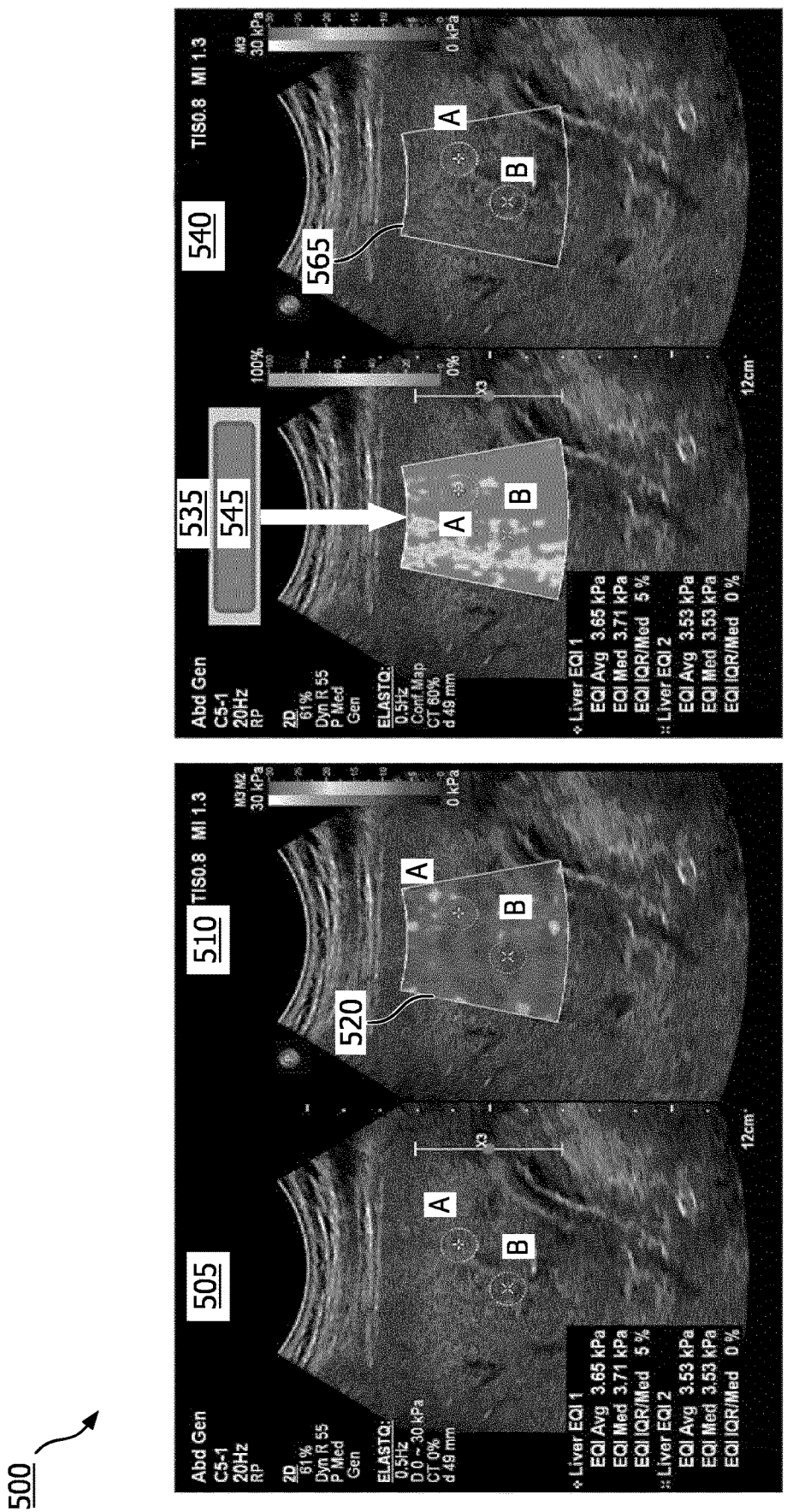
FIG. 5 shows another a series of example screen shots ultrasound images and example graphical overlays according to embodiments of the disclosure.

FIG. 5 shows another a series of example screen shots 500 ultrasound images 505, 510, 535, and 540 and example graphical overlays 520, 545, and 565 according to embodiments of the disclosure. Briefly, the far left image 505 is an ultrasound image of the liver and the middle left image 510 is the ultrasound image with a graphical overlay of tissue stiffness values 520 superimposed. In this example series 500, the patient moved during the imaging. An inexperienced user may not recognize that the image is overwhelmed by motion artifacts and should be reacquired. However, as seen in the middle right image 535, the confidence map 545 shows that nearly the entire region has low confidence values. The masked graphical overlay 565 of tissue stiffness values displayed on the far right image 540 shows that nearly all of the tissue stiffness values are masked out. Neither pointer A or B is on a valid data point. Both the confidence map and the masked graphical overlay provide feedback to the user that the image should be reacquired.

In another example, not shown, if a user selects an incorrect range estimate for tissue stiffness values, the confidence map will display a majority of low confidence values and a majority of tissue stiffness values will be masked out in the graphical overlay. This may alert the user that one or more settings of the ultrasound imaging system should be adjusted. In another example, if a rib casts a "shadow" over a portion of the image, the confidence map will display low confidence values in the area of the shadow, alerting the user to the obstruction. The rib may be detected because it is outside the estimated tissue stiffness value range and/or another detection method such as low displacement amplitude of shear waves.

Confidence maps and/or masked graphical overlays of tissue stiffness values may provide feedback to user on the quality of images and/or measurements. The feedback may be especially useful to inexperienced users who may be unfamiliar with anatomical landmarks and/or have difficulty recognizing image artifacts. The feedback may also alert users when they have inadvertently input incorrect settings for a shear wave imaging exam (e.g., forgot to change settings when examining a different type of tissue). The confidence maps and/or masked graphical overlays of tissue stiffness values may assist users in acquiring more accurate measurements. This may allow for more reliable patient diagnosis, monitoring, and/or reduction in the number of biopsies required.

Although not always shown, the images 105, 110, 405, 410, 435, 440, 505, 510, 535, and/or 540 may be shown on displays, such as display 238 shown in FIG. 2, may also illustrate user selections which may include, for example, icons or menu items which may be selected by the user to, for example, scan, file, print, transfer images (e.g., from one display to another), mute, transcribe, and/or use a headpiece, as desired. Further, one or more menus as is known in the art may be provided for a user's convenience. The displayed images and associated data may be saved at any time during an exam or during subsequent analysis. In some embodiments, a history mode may be activated to gather information indicative of when data may have been added and/or edited so that a user may refer back to original information and/or determine when and/or who made certain changes to information which may be saved in, for example, a generated report. Further, the changes may also be stored for later use.

Although the present system has been described with reference to an ultrasound imaging system, the present system may be extended to other ultrasound transducers. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications related to ultrasound-guided interventions and other interventions which may be guided by real-time medical imaging. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is confidence in tissue stiffness measurements by ultrasound transducers and method of operation thereof is provided. Another advantage of the present systems and method is that conventional medical imaging systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
    an ultrasound imaging device configured to generate shear wave signals responsive to shear wave tracking echoes received by an ultrasound probe communicatively coupled to the ultrasound imaging device; and
    a processor integral with or communicatively coupled to the ultrasound imaging device, wherein the processor includes:
        a shear wave processor configured to calculate tissue stiffness values based, at least in part, on the shear wave signals;
        an image processor configured to generate an ultrasound image including a graphical overlay of tissue stiffness values for one or more pixels within a region of interest, and
    a confidence map generator configured to calculate a plurality of confidence factors for each of a plurality of pixels of the ultrasound image, and calculate a confidence value for each of the pixels based on the plurality of confidence factors, wherein each confidence value has a value between 0 and 1;
    wherein the ultrasound image is configured to provide, based on the calculated confidence values, an indication of reliability of the tissue stiffness values within the region of interest, and
    wherein calculating the confidence value for each of the plurality of pixels comprises comparing the plurality of confidence factors and selecting a minimum confidence factor as the confidence value.

2. The ultrasound imaging system of claim 1, wherein the image processor is further configured to generate a masked graphical overlay of tissue stiffness values, wherein tissue stiffness values having a confidence value below a threshold value are masked out.

3. The ultrasound imaging system of claim 2, wherein the threshold value is set by a user.

4. The ultrasound imaging system of claim 2, further comprising a display communicatively coupled to the image processor, wherein, responsive to the image processor, the display is configured to display concurrently:
    the image with the masked graphical overlay of tissue stiffness values superimposed; and
    the image with a confidence map superimposed, wherein the confidence map is based, at least in part, on the confidence values.

5. The ultrasound imaging system of claim 2, wherein the ultrasound imaging system prevents collection of tissue stiffness values where the confidence values are below the threshold value.

6. The ultrasound imaging system of claim 1, wherein the tissue stiffness values are represented by different colors in the graphical overlay.

7. The ultrasound imaging system of claim 1, wherein the confidence factor is one of signal-to-noise ratio, motion detection, displacement amplitude, a range estimate of expected tissue stiffness values, or energy ratio, the energy ratio corresponding to a ratio of the energy of a noise-filtered shear wave signal to the energy of the corresponding unfiltered shear wave signal.

8. The ultrasound imaging system of claim 7, wherein the range estimate is set by a user.

9. The ultrasound imaging system of claim 7, wherein motion detection includes at least one of flash and flow.

10. The ultrasound imaging system of claim 1, wherein the ultrasound probe is further configured to perform B-mode imaging.

11. A method comprising:
    acquiring a shear wave image with an ultrasound probe of an ultrasound imaging system;
    calculating, with at least one processor of the ultrasound imaging system, a tissue stiffness value for each pixel in the shear wave image;
    calculating, with the at least one processor a plurality of confidence factors for each of the plurality of pixels, wherein each confidence value has a value between 0 and 1;
    determining, with the at least one processor, a confidence value for each of the plurality of pixels based, at least in part, on the corresponding plurality of confidence factors, wherein the confidence values correspond to confidence in tissue stiffness values;
    generating, with the at least one processor a confidence map based, at least in part, on the confidence values, wherein calculating the confidence value for each of the plurality of pixels comprises comparing the plurality of confidence factors and selecting a minimum confidence factor as the confidence value; and
    displaying the confidence map on a display of the ultrasound imaging system.

12. The method of claim 11, wherein each of the plurality of confidence factors is weighted.

13. The method of claim 11, wherein a subset of the plurality of confidence factors are compared to determine the confidence values.

14. The method of claim 13, wherein the subset of the plurality of confidence factors is selected by a user.

15. The method of claim 11, wherein the confidence map represents different confidence values with different colors.

\* \* \* \* \*